(12) United States Patent
Cossy et al.

(10) Patent No.: US 6,515,127 B1
(45) Date of Patent: Feb. 4, 2003

(54) METHOD FOR PREPARING QUINOLINE-5,8-DIONES

(75) Inventors: Janine Cossy, Paris (FR); Damien Belotti, Couvrot (FR)

(73) Assignee: Laboratoire L. Lafon, Maisons Alfort (FR)

( * ) Notice: Subject to any disclaimer, the term of this patent is extended or adjusted under 35 U.S.C. 154(b) by 246 days.

(21) Appl. No.: 10/049,375

(22) PCT Filed: Aug. 10, 2000

(86) PCT No.: PCT/FR00/02295

§ 371 (c)(1),
(2), (4) Date: Feb. 12, 2002

(87) PCT Pub. No.: WO01/12597

PCT Pub. Date: Feb. 22, 2001

(30) Foreign Application Priority Data

Aug. 13, 1999 (FR) .............................. 99 10491

(51) Int. Cl.$^7$ .................... C07D 215/60; C07D 215/16; C07D 215/38; C07D 215/46
(52) U.S. Cl. ................. 546/153; 546/155; 546/156; 546/157; 546/159; 546/162; 546/178
(58) Field of Search ................. 546/153, 155, 546/156, 157, 159, 162, 178

(56) References Cited

U.S. PATENT DOCUMENTS 4,692,449 A * 9/1987 Medwid
4,742,059 A * 5/1988 Medwid

FOREIGN PATENT DOCUMENTS

| CA | 2029421 | * | 5/1991 |
| EP | 0 433 679 | | 6/1991 |
| WO | 2000055160 | * | 9/2000 |

OTHER PUBLICATIONS

Babu, CA 69:10339, abstract of Symp Syn Heterocycl, Compounds Physiol Interest, Hyderabad, India, 1966.*
Babu, CA 71:3232, abstract, 1968.*
Pascual–Alfonso, CA 133:43466, 2000.*
By P. Withopf et al., "Synthese Von 8–Azajuglon (4–Hy–droxy–5, 8–Chinolinchinon)", Tetrahedron, vol. 43, No. 20, 1997, pp. 4549–4554.

By K.T. Potts et al., "Cycloaddition Routes to Azaanthraquinone Derivatives. Use of Azadienophiles", Journal of Organic Chemistry, vol. 51, No. 11, 1986, pp. 2011–2021.
By C. Temple, Jr. et al., "Synthesis of Potential Antimalarial Agents. Preparation of Some 6–Amino–5,8–dimethoxyquinolines and the Corresponding 6–Amino–5, 8–quinolinediones", Journal of Medicinal Chemistry, vol. 17, No. 6, 1974, pp. 615–619.
Chemical Abstracts and Database Chemical Abstracts, Nos. XP–002139244 and XP–002139245, vol. 69, No. 3, Jul. 15. 1968.
By G. Matsuo et al., "Two–step synthesis of C–glycosyl juglones from unprotected sugars: a novel approach to angucycline antibiotics", Chemical Communications, 1996, pp. 2173–2174.
By S. Ghosh et al., "[4+2]–Cycloaddition reactions employing 2–fluoro–2–alkenal N,N–dimethylhydrazones: synthesis of 3–fluoropyridines and dihydro or tetrahydro derivatives thereof", Journal of Fluorine Chemistry, vol. 67, No. 1, 1994, pp. 53–56.
By M. Croisy–Delcey et al., "Synthesis of 4–amino–substituted–6–hydroxy and 11–hydroxy–naphtho (2,3–g)quinoline–5,12–diones . . . ", Journal of Heterocyclic Chemsitry, vol. 30, No. 1, 1993, pp. 55–60.
By C. Avendano et al., "A Comparative Study of Synthetic Approaches to 1–Methyl–2,5,8 (1H)–quinolinetrione and 4–Methyl–2,5,8 (1H)–quinolinetrione", Synthesis, 1991, pp. 727–730.

* cited by examiner

Primary Examiner—D. Margaret Seaman
(74) Attorney, Agent, or Firm—Young & Thompson

(57) ABSTRACT

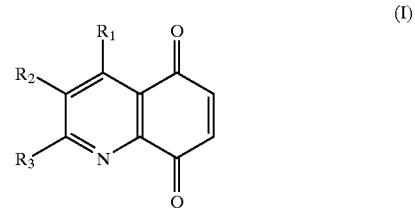

(I)

The invention concerns a method for preparing quinoline-5,8-diones of formula (I) wherein $R_1$, $R_2$ and $R_3$ are as defined in claim 1, by light-induced oxygenation of a 8-hydroxyquinoline.

5 Claims, No Drawings

METHOD FOR PREPARING QUINOLINE-5,8-DIONES

This application is a 371 of PCT/FR00/02295, filed Aug. 10, 2000.

The present invention relates to a process for preparing quinoline-5,8-diones which find an application as intermediate products, especially in the pharmaceutical industry.

Bracher (Heterocycles, 29, 2093, 1989) has already mentioned a process for preparing quinoline-5,8-dione from 5-amino-8-hydroxyquinoline by oxidation with dichromate. This process requires a double functionalization of the quinoline nucleus, and thus involves starting materials that are expensive and not readily available. S. Ghosh (J. Fluorine Chem., 1994; 67: 53–56) describes quinoline-5,8-dione derivatives obtained by cycloaddition between p-benzoquinone and a substituted diene. 4-Chloroquinoline-5,8-dione is described as a synthetic intermediate of more complex tricyclic or tetracyclic compounds (M. Croisy-Delsey et al., J. Heterocyclic Chem. 1993; 30: 55–60), whereas 2-methoxyquinoline-5,8-dione is presented as a by-product of the N-alkylation of 2,5,8(1H)-quinolinetrione (C. Avendano et al. Synthesis 1991; 727–730). 4-Hydroxy-5,8-quinolinequinone may be synthesized from 2,5-dimethoxyaniline and from the ester of methylacrylic acid (P. Withopf et al. Tetrahedron, 1987; 43(20):4549–4554). Quinoline-5,8-dione and 2-chloro-4-methylquinoline-5,8-dione are starting materials used in the synthesis of azaanthraquinone derivatives (K. T. Potts et al., J. Org. Chem., 1986:2011–2021). Antimalaria agents derived from 6-amino-5,8-dimethoxyquinolines are prepared from 2-trifluoro-4-methyl or from 2,4-dimethyl quinoline-5,8-dione (C. Temple et al., J. Med. Chem., 1974; 17(6):615–619). Finally, EP 0 433 679 describes quinoline-5,8-dione derivatives as inhibitors of the Maillard reaction in the body, this reaction being responsible (by denaturing proteins via sugars) for several consequences of diabetes (neuropathy, retinopathy, etc.).

Methods also exist for preparing quinones by photo-oxidation of phenols (for example Chem. Comm., 2173, 1996), but it has never been envisaged to apply such methods to heterocyclic compounds and in particular to quinoline derivatives.

The reason for this is that it was not obvious that such methods would not be hampered by the presence of the electron-withdrawing pyridine nucleus. Reactions between the quinones and the nitrogen of the pyridine nucleus, leading to colored polymers, could also have been feared. This is what was observed with 5-hydroxyisoquinoline.

It has now been found that a particular group of 8-hydroxyquinolines gives, by photo-oxidation, in the presence of a sensitizer and decomposition of the intermediate hydroxyperoxide, quinoline-5,8-diones in high yields.

One subject of the present invention is a process for preparing quinoline-5,8-diones of formula:

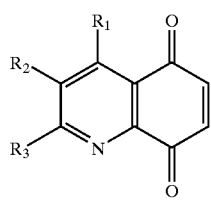

(I)

in which:

$R_1$, $R_2$ and $R_3$ are chosen from hydrogen, a halogen atom, a $C_1$–$C_6$ alkyl group, —CHO, —OH, —OR, —COOH, —CN, —CO$_2$R, —CONHR, —CONRR'—, —NH$_2$, —NHCOR,

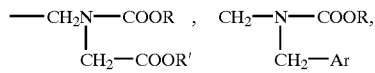

morpholino and SO$_3$H, R and R' being chosen from $C_1$–$C_6$ alkyl groups and Ar being a $C_6$–$C_{14}$ aryl group, in which an 8-hydroxyquinoline of formula:

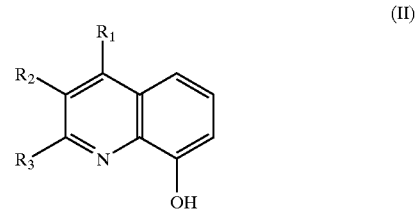

(II)

in which $R_1$, $R_2$ and $R_3$ have the meaning given above, is oxidized with oxygen under the action of actinic radiation in solution in an organic solvent and in the presence of a catalytic amount of a sensitizer, and the hydroperoxide formed, of formula:

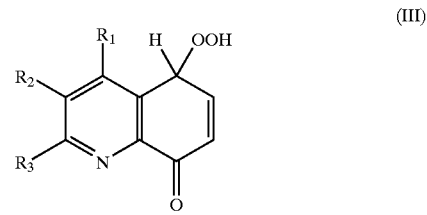

(III)

is then decomposed to a compound of formula I.

The oxidation reaction with oxygen is carried out in an organic solvent in which the starting 8-hydroxyquinoline of formula II is soluble. The solvent is advantageously chosen such that the sensitizer is also soluble therein.

The sensitizer may especially be tetraphenylporphine (or TPP), in which case the solvent may especially be dichloromethane.

Other suitable sensitizers and solvents may also be used, and in particular:

rose bengal in CH$_3$CN, MeOH, EtOH, CHCl$_3$ or water;

methylene blue in CH$_3$CN, MeOH, EtOH, CHCl$_3$ or water;

tetra(4-pyridyl)porphine in CH$_2$Cl$_2$ or CHCl$_3$;

dicyanonaphthalene (DCN), dicyanoanthracene (DCA) or dicyanobenzene (DCB);

N,N'-dimethyl-2,7-diazapyrenium (DAP$^{2+}$) bis (tetrafluoroborate).

The reaction is advantageously carried out in the region of room temperature (15 to 25° C.) under irradiation, with visible light while sparging with oxygen, for a period which may be from 2 to 8 hours.

The hydroperoxide formed, of formula III, spontaneously decomposes with stirring, especially in the presence of Na$_2$SO$_4$.

A subject of the present invention is also the quinoline-5,8-diones of formula:

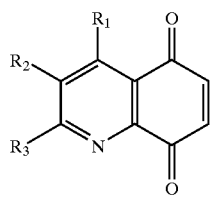

in which:

R₁, R₂ and R₃ are chosen from hydrogen, a halogen atom, a $C_1$–$C_6$ alkyl group, —CHO, —OH, —OR, —COOH, —CN, —CO₂R, —CONHR, —CONRR'—, —NH₂, —NHCOR,

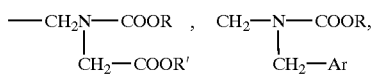

morpholino and SO₃H, R and R' being chosen from $C_1$–$C_6$ alkyl groups and Ar being a $C_6$–$C_{14}$ aryl group, with the exception of the compounds in which:

R₁=H, R₂=H and R₃ is chosen from H, CH₃, CN and CHO,

R₁=H or CH₃, R₂=F and R₃=H p1 R₁=Cl, R₂=H and R₃=H

R₁=OH, R₂=H and R₃=COOH, COOCH₃ or CH₃

R₁=OH, R₂=COOH or COOC₂H₅ and R₃=H

R₁=H, R₂=H and R₃=OCH₃

R₁=OH, R₂=H and R₃=H

R₁=OCH₃, R₂=H and R₃=H

R₁=CH₃, R₂=H and R₃=Cl

R₁=CH₃, R₂=H and R₃=CH₃

EXAMPLES

Examples of the implementation of the process according to the present invention will be given below.

General Procedure

A solution of the compound of formula II (2 mmol) in dichloromethane (or another solvent if insoluble) (20 ml) in a Pyrex flask with flat faces, containing a catalytic amount of tetraphenylporphine (TPP, 6 mg, i.e. 0.5 mol %), is irradiated at 20° C. (cooling with water) with visible light (1500 W xenon arc, filter for radiations>495 nm) while sparging with oxygen, for 2–8 hours (the reaction is monitored by TLC). The irradiated solution is then poured onto dry Na₂SO₄ (3 g), stirred at room temperature for 12 hours and filtered. The solvent is evaporated off and the crude quinone obtained is purified by chromatography on a column of silica.

The characteristics of the various implementations are collected in the table below.

| Example | Compound II | Solvent | Time | Compound II recovered % |
|---|---|---|---|---|
| 1 | 8-hydroxyquinoline | CH₂Cl₂ | 2 h 30 | / |
| 2 | 8-hydroxy-2-methylquinoline | CH₂Cl₂ | 2 h 30 | / |
| 3 | 8-hydroxy-2-cyanoquinoline | CH₂Cl₂ | 8 h | 15% |
| 4 | 8-hydroxy-2-formylquinoline | CH₂Cl₂ | 5 h 30 | 25% |
| 5 | 8-hydroxy-2-methoxycarbonylquinoline | CH₂Cl₂ | 2 h | / |

-continued

| | Structure | Solvent | Time | Yield |
|---|---|---|---|---|
| 6 | 8-hydroxyquinoline-2-carboxylic acid N,N-diisopropylamide | CH₂Cl₂ | 2 h | / |
| 7 | 8-hydroxyquinolin-2-yl-methyl-N-benzyl-N-Boc | CH₂Cl₂ | 2 h 30 | / |
| 8 | 8-hydroxyquinolin-2-yl-methyl-N-(CO₂Me)-N-Boc | CH₂Cl₂ | 2 h | 21% |
| 9 | 4-methyl-8-hydroxyquinoline | CH₂Cl₂ | 2 h | / |
| 10 | 3-methyl-8-hydroxyquinoline | CH₂Cl₂ | 2 h | / |
| Comparative example | 2-(hydroxymethyl)-8-hydroxyquinoline | CH₂Cl₂ | 2 h | >80% |

| Example | Compound I | Yield (purification on SiO₂) | Yield relative to the converted substrate |
|---|---|---|---|
| 1 | quinoline-5,8-dione | 82% (95% crude ≈ clean) | 82% |
| 2 | 2-methylquinoline-5,8-dione | 80% (98% crude ≈ clean) | 80% |

-continued
| | | | |
|---|---|---|---|
| 3 | 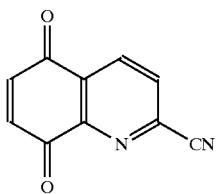 | 73% | 86% |
| 4 | 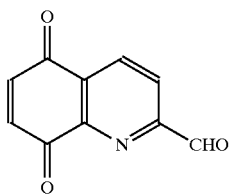 | 51% | 68% |
| 5 | 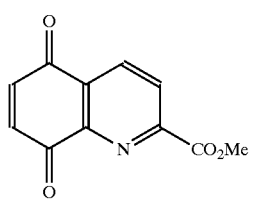 | 81% | 81% |
| 6 | 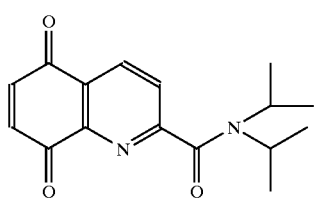 | 89% | 89% |
| 7 | 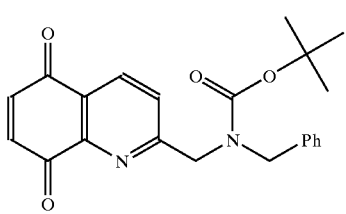 | 53% | 53% |
| 8 | 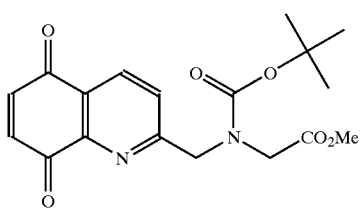 | 50% | 63% |
| 9 | 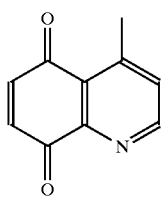 | 72% | 72% |

| | -continued | | |
|---|---|---|---|
| 10 | ![structure: 3-methylquinoline-5,8-dione] | 82% | 82% |
| Comparative example | | / | / |

The characteristics of the products obtained will be given below.

Product of example 1:
  dark yellow solid; m.p.=120–122° C.
  IR (CHCl$_3$):1670 cm$^{-1}$
  $^1$H NMR 300 MHz (CDCl$_3$): δ 7.08 (d, 1H, J=11 Hz); 7.18 (d, 1H, J=11 Hz); 7.73 (m; 1H); 8.44 (m, 1H); 9.07 (m, 1H)) ppm
  $^{13}$C NMR 75 MHz (CDCl$_3$): δ 127.9 (d); 129.1 (s); 134.6 (d); 138.0 (d); 139.1 (d); 147.4 (s); 154.8 (d); 183.2 (s); 184.5 (s) ppm.
  MS C$_9$H$_5$NO$_2$ (relative intensity): m/z 159 (M$^+$, 100); 131 (25); 103 (51).

Product of example 2:
  dark yellow solid; m.p.=135–140° C. (decomp.)
  IR (CHCl$_3$): 1670 cm$^{-1}$
  $^1$H NMR 300 MHz (CDCl$_3$): δ 2.80 (s, 3H); 7.03 (d, 1H, J=11 Hz); 7.13 (d, 1H, J=11 Hz); 7.58 (d, 1H, J=8 Hz); 8.30 (d, 1H, J=8 Hz) ppm.
  $^{13}$C NMR 75 MHz (CDCl$_3$): δ 25.3 (q); 127.0 (s); 127.8 (d); 134.6 (d); 137.9 (d); 138.8 (d); 146.9 (s); 165.2 (s); 183.5 (s): 184.6 (s) ppm.

Product of example 3:
  dark green-yellow solid; m.p.=170–172° C.
  IR (CHCl$_3$): 2250; 1680 cm$^{-1}$
  $^1$H NMR 300 MHz (CDCl$_3$): δ 7.20 (d, 1H, J=11 Hz); 7.30 (d, 1H, J=11 Hz); 8.12 (d, 1H, J=8 Hz); 8.64 (d, 1H, J=8 Hz) ppm
  $^{13}$C NMR 75 MHz (CDCl$_3$): δ 115.7 (s); 130.1 (s); 131.9 (d); 136.4 (d); 138.2 (s); 138.3 (d); 139.7 (d); 147.9 (s); 181.1 (s); 182.8 (s) ppm.

Product of example 4:
  dark green-yellow solid; m.p.=185–187° C.
  IR (CHCl$_3$): 1720; 1680 cm$^{-1}$
  $^1$H NMR 300 MHz (CDCl$_3$): δ 7.20 (d, 1H, J=11 MHz); 7.30 (d, 1H; J=11 Hz); 8.34 (d, 1H, J=8 Hz); 8.65 (d, 1H, J=8 Hz); 10.32 (s, 1H) ppm.
  $^{13}$C NMR 75 MHz (CDCl$_3$): δ 124.9 (d); 131.2 (s); 136.4 (d); 138.3 (d); 139.6 (d); 147.6 (s); 155.5 (s); 182.4 (s); 183.6 (s); 191.8 (d) ppm.
  MS C$_{10}$H$_5$NO$_3$ (relative intensity): m/z 187 (M$^+$, 17); 159 (100); 103 (32).

Product of example 5:
  $^1$H NMR 300 MHz (CDCl$_3$): δ 4.07 (s, 3H); 7.16 (d, 1H, J=10.5 Hz); 7.27 (d, 1H, J=10.5 Hz); 8.50 (d, 1H, J=8.1 Hz); 8.61 (d, 1H, J=8.1 Hz) ppm.

Product of example 6:
  $^1$H NMR 300 MHz (CDCl$_3$): δ 1.25 (d, 6H, J=7.2 Hz); 1.55 (d, 6H, 7.2 Hz); 3.62 (sept, 1H, J=7.2 Hz); 3.82 (sept., 1H, J=7.2 Hz); 7.07 (d, 1H, J=10.5 Hz); 7.17 (d, 1H, J=10.5 Hz); 7.88 (d, 1H, J=8.2 Hz); 8.49 (d, 1H, J=8.2 Hz) ppm.

Product of example 7:
  $^1$H NMR 300 MHz (CDCl$_3$): (2 rotamers≈50:50) δ 1.40 and 1.50 (s, 9H); 4.50 and 4.55 (s, 2H); 4.70 and 4.77 (s, 2H); 7.03 (d, 1H, J=10.5 Hz); 7.14 (d, 1H, J=10.5 Hz); 7.15–7.35 (m, 5H); 7.48 and 7.61 (d, 1H, J=8.2 Hz); 8.33 (d, 1H, J=8.2 Hz) ppm.

Product of example 8:
  $^1$H NMR 300 MHz (CDCl$_3$): (2 rotamers≈50:50) δ 1.40 and 1.47 (s, 9H); 3.70 and 3.72 (s, 3H); 4.02 and 4.13 (s, 2H); 4.80 and 4.83 (s, 2H); 7.04 and 7.06 (d, 1H, J=10.5 Hz); 7.13 and 7.15 (d, 1H, J=10.5 Hz); 7.89 and 7.91 (d, 1H, J=8.3 Hz); 8.42 and 8.45 (d, 1H, J=8.3 Hz) ppm.

Product of example 9:
  $^1$H NMR 300 MHz (CDCl$_3$): δ 2.81 (s, 3H); 7.00 (d, 1H, J=10.4 Hz); 7.11 (d, 1H, J=10.4 Hz); 7.48 (d, 1H, J=4.9 Hz); 8.86 (d, 1H, J=4.9 ppm).
  MS [C$_{10}$H$_7$NO$_2$] (relative intensity): m/z 173 (M$^+$, 100); 145 535); 117 (23); 91 (28).

Product of example 10:
  $^1$H NMR 300 MHz (CDCl$_3$): δ 2.55 (s, 3H); 7.04 (d, 1H, J=10.4 Hz); 7.14 (d, 1H, J=10.4 Hz); 8.20 (s, 1H); 8.88 (s, 1H) ppm
  MS [C$_{10}$H$_7$NO$_2$] (relative intensity): m/z 173 (M$^+$, 100); 145 (23); 117 (34); 91 (28).

It is seen that the success of the process depends strictly on the nature of the starting materials. Thus, for example, a compound of formula II in which R$_3$ is a —CH$_2$OH group is not converted into a product of the formula I, but instead leads to a brown coloration and to polymerization.

What is claimed is:
1. A process for preparing quinoline-5,8-diones of the formula:

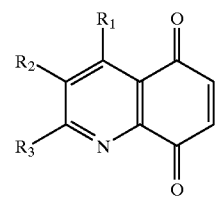

(I)

in which:
  R$_1$, R$_2$ and R$_3$ are chosen from hydrogen, a halogen atom, a C$_1$–C$_6$ alkyl group, —CHO, —OH, —OR, —COOH, —CN, —CO$_2$R, —CONHR, —CONRR'—, —NH$_2$, —NHCOR,

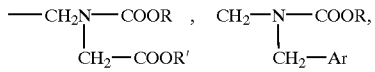

morpholino and SO$_3$H, R and R' being chosen from C$_1$–C$_6$ alkyl groups and Ar being a C$_6$–C$_{14}$ aryl group, in which an 8-hydroxyquinoline of formula:

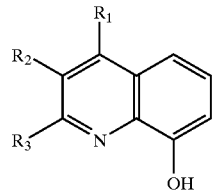

(II)

in which R$_1$, R$_2$ and R$_3$ have the meaning given above, is oxidized with oxygen under the action of actinic radiation in solution in an organic solvent and in the presence of a catalytic amount of a sensitizer, and the hydroperoxide formed, of formula:

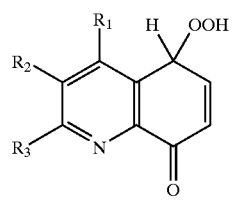

(III)

is then decomposed to a compound of formula I.

2. The process as claimed in claim 1, in which the sensitizer is tetraphenylporphine.

3. The process as claimed in claim 1, in which the solvent is dichloromethane.

4. A quinoline-5,8-dione of the formula:

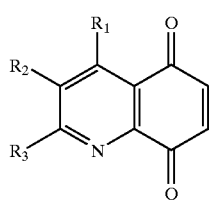

in which:

R$_1$, is chosen from hydrogen, a halogen atom, a —CHO, —OR, —COOH, —CN, —CO$_2$R, —CONHR, —CONRR'—, —NH$_2$, —NHCOR,

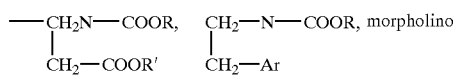

and SO$_3$H, R and R' being chosen from C$_1$–C$_6$ alkyl groups and Ar being a C$_6$–C$_{14}$ aryl group, R$_2$ is chosen from hydrogen, a halogen atom, a —CHO, —OH, —OR, —COOH, —CN, —CONHR, —CONRR', —NH$_2$, —NHCOR,

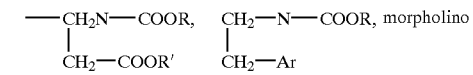

and SO$_3$H, R and R' being chosen from C$_1$–C$_6$ alkyl groups and Ar being a C$_6$–C$_{14}$ aryl group, R$_3$ is chosen from hydrogen, a halogen atom, a C$_1$–C$_6$ alkyl group, —CHO, —OR, —COOH, —CN, —CONHR, —CONRR'—, —NH$_2$, —NHCOR,

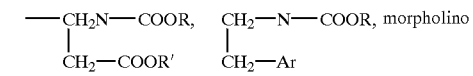

and SO$_3$H, R and R' being chosen from C$_1$–C$_6$ alkyl groups and Ar being a C$_6$–C$_{14}$ aryl group, with the exception of the compounds in which:

R$_1$=H, R$_2$=H and R$_3$ is chosen from H, CH$_3$, CN and CHO
R$_1$=H or CH$_3$, R$_2$=F and R$_3$=H
R$_1$=Cl, R$_2$=H and R$_3$=H
R$_1$=OH, R$_2$=H and R$_3$=COOH, COOCH$_3$ or CH$_3$
R$_1$=OH, R$_2$=COOH or COOC$_2$H$_5$ and R$_3$=H
R$_1$=H, R$_2$=H and R$_3$=OCH$_3$
R$_1$=OH, R$_2$=H and R$_3$=H
R$_1$=OCH$_3$, R$_2$=H and R$_3$=H
R$_1$=CH$_3$, R$_2$=H and R$_3$=Cl
R$_1$=CH$_3$, R$_2$=H and R$_3$=CH$_3$.

5. A quinoline-5,8-dione of the formula:

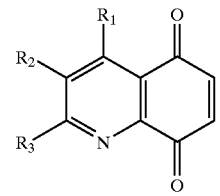

in which:

R$_1$, R$_2$ are chosen from hydrogen, a halogen atom, a C$_1$–C$_6$ alkyl group, —CHO, —OH, —OR, —COOH, —CN, —CO$_2$R, —CONHR, —CONRR'—, —NH$_2$, —NHCOR,

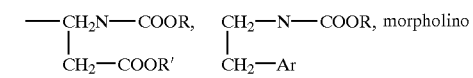

and SO$_3$H, R and R' being chosen from C$_1$–C$_6$ alkyl groups and Ar being a C$_6$–C$_{14}$ aryl group, R$_3$ is chosen from the groups CONRR' and

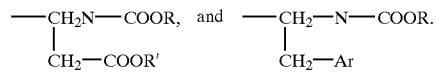

* * * * *